US009256285B2

(12) United States Patent
Leroy et al.

(10) Patent No.: US 9,256,285 B2
(45) Date of Patent: Feb. 9, 2016

(54) METHOD FOR GAZE-CONTROLLED TEXT SIZE CONTROL, AND METHODS FOR GAZE-BASED MEASURING OF A TEXT READING SPEED AND OF A NUMBER OF VISUAL SACCADES PER TEXT LINE

(75) Inventors: Arnaud Leroy, Vahl-Ebersing (FR); Julien Fleureau, Rennes (FR); Philippe Guillotel, Vern sur Seiche (FR)

(73) Assignee: THOMPSON LICENSING SA, Issy les Moulineaux (FR)

( * ) Notice: Subject to any disclaimer, the term of this patent is extended or adjusted under 35 U.S.C. 154(b) by 47 days.

(21) Appl. No.: 14/239,360

(22) PCT Filed: Aug. 10, 2012

(86) PCT No.: PCT/EP2012/065758
§ 371 (c)(1),
(2), (4) Date: Jun. 17, 2014

(87) PCT Pub. No.: WO2013/026725
PCT Pub. Date: Feb. 28, 2013

(65) Prior Publication Data
US 2014/0327609 A1    Nov. 6, 2014

(30) Foreign Application Priority Data
Aug. 19, 2011   (EP) .................................... 11290378

(51) Int. Cl.
*G06F 3/01*     (2006.01)
*G06F 17/21*    (2006.01)
(Continued)

(52) U.S. Cl.
CPC ................ *G06F 3/013* (2013.01); *A61B 5/726* (2013.01); *G06F 3/015* (2013.01); *G06F 17/148* (2013.01); *G06F 17/214* (2013.01)

(58) Field of Classification Search
CPC ....... G06F 3/013; G06F 3/015; G06F 17/148; G06F 17/00–17/156; A61B 5/726
See application file for complete search history.

(56) References Cited

U.S. PATENT DOCUMENTS 5,886,683 A *  3/1999  Tognazzini et al. ........... 715/700
6,873,314 B1    3/2005  Campbell
(Continued)

FOREIGN PATENT DOCUMENTS

CN    101707056    5/2010
EP      0816984    1/1998
(Continued)

OTHER PUBLICATIONS

Young et al: "Eye-movement measurement techniques", Encyclopedia of Medical Devices and Instrumentation,ed. JG Webster, pp. 315-330, John Wiley, New York (1975).
(Continued)

*Primary Examiner* — Sanjiv D Patel
(74) *Attorney, Agent, or Firm* — Meagher Emanuel Laks; Goldberg & Liao, LLP

(57) ABSTRACT

For gaze-controlled text size control of a display, the invention proposes to probe, sample and record a user's horizontal gaze Signal; to subject the gaze Signal to a subband filterbank or wavelet transform; to detect line delimiters in the gaze Signal; to derive a reading speed; to determine, as a number of saccades per text line the number of locations where the gaze Signal has sudden high slope portions surrounded on both sides by portions of markedly smaller slope; to detect, based on the reading speed and the number of saccades, a too small font size Status or a too big font size Status; and to initiate a corresponding font size change. Parts of this method can be used for gaze-based measuring of text reading speed and for gaze-based measuring of number of saccades.

6 Claims, 3 Drawing Sheets

(51) Int. Cl.
G06F 17/14 (2006.01)
A61B 5/00 (2006.01)

(56) References Cited

U.S. PATENT DOCUMENTS

| | | | |
|---|---|---|---|
| 8,643,680 B2* | 2/2014 | Baldwin et al. | 345/684 |
| 2006/0270945 A1* | 11/2006 | Ghajar | 600/558 |
| 2009/0225278 A1 | 9/2009 | Chen | |
| 2009/0289895 A1 | 11/2009 | Nakada et al. | |
| 2009/0292223 A1* | 11/2009 | Sugio et al. | 600/558 |
| 2010/0191140 A1* | 7/2010 | Terada et al. | 600/544 |
| 2011/0148931 A1 | 6/2011 | Kim | |
| 2011/0170067 A1* | 7/2011 | Sato et al. | 351/209 |
| 2014/0253437 A1* | 9/2014 | Vaught et al. | 345/156 |

FOREIGN PATENT DOCUMENTS

| | | |
|---|---|---|
| EP | 2050389 | 4/2009 |
| KR | 100741426 | 7/2007 |
| WO | WO03050658 | 6/2003 |
| WO | WO2010018459 | 2/2010 |

OTHER PUBLICATIONS

Search Report Dated Jan. 2, 2013.

Bulling et al.: "Robust Recognition of Reading Activity in Transit Using Wearable Electrooculography", May 19, 2008, Pervasive Computing; [Lecture Notes in Computer Science], pp. 10-37.

Beymer et al.: "An eye tracking study of how font size and type influence online reading", Proceedings of the 22ndBritish HCI Group Annual Conference vol. 2 Dec. 31, 2008, pp. 15-18.

A.Bulling et al: "Eye Movement Analysis for Activity Recognition Using Electrooculography", IEEE , vol. 33, No. 4, Apr. 1, 2011,pp. 741-753.

Deng L Y et al: "EOG-based signal detection and verification for HCI", Machine Learning and Cybernetics, 2009 International Conference on, IEEE, Piscataway, NJ, USA, Jul. 12, 2009, pp. 3342-3348.

"Eagle Eyes project", bc.edu Boston College; Jun. 16, 2011.

Mizutan et al, "Single Line Reader", Tohoku University, cmsoft.com.br/sir/.

International Society for Clinical Electrophysiology of Vision (ICSEV), "Visual Electrodiagnostics—A Guide to Procedures", pp. 1-14.

Miyashita et al: "Implementation of EOG-based Gaze Estimation in HMD with Head-tracker", 18th International Conference on Artificial Reality and Telexistence (ICAT 2008), Dec. 1-3, 2008.

Mark J. Shensa: "The Discrete Wavelet Transform: Wedding the Â Trous and Mallat Algorithms", IEEE Transactions on Signal Processing, vol. 40 No. 10, pp. 2464-2482, Oct. 1992.

Tobii: "Unveils the world's first eye controlled laptop", Jun. 16, 2011.

* cited by examiner

METHOD FOR GAZE-CONTROLLED TEXT SIZE CONTROL, AND METHODS FOR GAZE-BASED MEASURING OF A TEXT READING SPEED AND OF A NUMBER OF VISUAL SACCADES PER TEXT LINE

This application claims the benefit, under 35 U.S.C. §365 of International Application PCT/EP2012/065758, filed Aug. 10, 2012, which was published in accordance with PCT Article 21(2) on Feb. 28, 2013 in English and which claims the benefit of European patent application No. 11290378.6, filed Aug. 19, 2011.

FIELD OF THE INVENTION

The present invention relates to human-machine interface, in particular to text size control on display devices.

BACKGROUND OF THE INVENTION

Recording and estimating the gaze path of a user watching a screen is a mature technology opening new perspectives in terms of Human-Machine Interfaces. Such captures are till now mainly achieved using infrared video technologies in commercial systems.

[5] purport to describe a laptop computer product with integrated eye control, taking advantage of the reflection of infrared sources on the user's eyes to estimate the current gaze orientation.

Other, more experimental systems are physiologically based on the recording of the corneo-retinal potential by the means of electrodes positioned around the eye. Two electrodes are generally used to record the horizontal movements, two others catch the vertical motions and a last one is used as a reference. FIG. 1 shows an example of a horizontal capture setup.

Young et al [1] have purportedly shown that captured signals, namely ElectroOculoGram (EOG) signals, are linearly correlated to the eye motions.

Several commercial or academic systems embed dedicated amplifiers to measure and record the associated signal. "BIOPAC" systems for an example of generic biomedical amplifier, "BlueGain EOG Amplifier" developed by Cambridge Research Systems, and an Eye-movement Tracking System proposed by Deng [2].

Even if such systems were historically and mainly used for medical purposes [3], recent developments in video games and entertainment [4] prove their potential as a new way for users to interact with a machine.

The Boston College "EagleEyes" Project [6] is an example of taking advantage of the EOG to help users with severe physical disabilities to control a computer.

In [7], Bulling et al propose to use EOG signals to recognize users' activities by analyzing their eyes movements. Horizontal EOGs are processed with dedicated wavelet transforms and help to determine if the user is reading, writing or browsing while s/he is in front of her/his computer.

With the development of e-books, the improvements of TV-screens which are now able to satisfyingly display texts and web pages, it becomes apparent that reading comfort may not always be optimal and depends among others on the size of the text font used in the display. To adjust font size to individual users' needs, [5] requires an active interaction of the user with the machine like a deliberate click on an icon, or a specific eye motion to zoom on some part of a screen. The Single Line Reader algorithm implementation in [8] also makes use of deliberate head movements to control the speed and scrolling direction of a single line text display.

An improvement of ease of user interaction is thus desirable.

Invention

The present invention proposes a gaze-based way to improve the user experience when watching multimedia content comprising text. More precisely, a gaze information is used to automatically adapt the text font size to enhance the user comfort. The invention is based on having recognized that reading a text with too small font requires more time and effort for a user than reading optimally-sized text; and on the other hand reading a text with too large font requires the gaze to move with bigger amplitudes, leading to an associated bigger eyestrain. According to the present invention, font size control is achieved by analyzing the user's eyes movements. This method is passive from the user's point of view, in the sense that it does not require any active user manipulation for font size change. Eye movement characteristics are recorded while users are reading a text, and are evaluated to automatically adapt the font size and thus enhance the visual comfort and the user experience.

A method for gaze-controlled text size control according to the present invention comprises the following steps:

A user's horizontal gaze signal is probed, sampled and recorded. The sampling is performed at a predefined sampling frequency. The horizontal gaze signal may be amplified and is processed for determining and analyzing the horizontal eyes movements as further described in the following. For the processing and analyzing, one may assume a reading context where a user sequentially reads a justified text from the left to the right and from the top to the bottom of a display screen. It can additionally be assumed that line returns, i.e. a repeated reading of a same line of text, or line jumps, i.e. the skipping of lines between lines that are read, do not occur.

The horizontal gaze signal may be calibrated so that amplitude values between 0 and 1 in the normalized signal matches the width of the entire display screen. In the following description, it is assumed that the arrangement of the electrodes at the head, together with the polarity of the probed gaze signal, the amplification and the calibration cooperate in such a way, that a value of 0 (zero) for the calibrated gaze signal corresponds to a gaze that is directed to the left border of the text block being read, and a value of 1 (one) for the calibrated gaze signal corresponds to a gaze that is directed to the right border of the text block. Transformation of these assumptions to other setups, like change of signal polarity or change of reading direction, is straightforward.

The horizontal gaze signal, optionally calibrated, is then subjected to a subband filter bank transform into several frequency bands, or to a wavelet transform on several levels of detail.

In the transformed horizontal gaze signal, line delimiters are detected. This can be achieved by locating pieces of the transformed horizontal gaze signal where selected ones of the frequency bands or wavelet levels of detail are below a first threshold.

Then, for each pair of consecutive line delimiters, a reading speed is derived from the distance in samples of the line delimiters, in relation to the sampling frequency of the horizontal gaze signal. This reading speed is a momentary value, and conceptually relates to the portion of the gaze signal that is enclosed between the line delimiters.

The horizontal gaze signal between the pair of consecutive line delimiters describes the eye movement while reading a current line of text. From this signal, a number of saccades in this line is determined by counting those locations, where the gaze signal has a sudden high slope portion surrounded on both sides by portions of markedly smaller slope. This analysis may be performed by comparing different frequency bands or time-frequency components of the transformed horizontal gaze signal. Saccades are elementary movements of the eye while scanning and reading a text.

If the number of saccades is above a second threshold, or if the reading speed is below a third threshold, this is detected as an indicator that the currently used font size is too small, and an increase of the font size is initiated.

On the other hand, if the number of saccades is less than a fourth threshold, this is detected as an indicator that the currently used font size is too big, and a decrease of the font size is initiated.

These steps are repeated for every line of text, i.e. for all pieces of the horizontal gaze signal between consecutive line delimiters.

DRAWINGS

Exemplary embodiments of the invention are illustrated in the drawings and are explained in more detail in the following description.

EXEMPLARY EMBODIMENTS

An example implementation of the method according to the present invention is described in the following. The ElectroOculoGram signal also denoted as EOG signal is used as a gaze signal.

Figure 1:
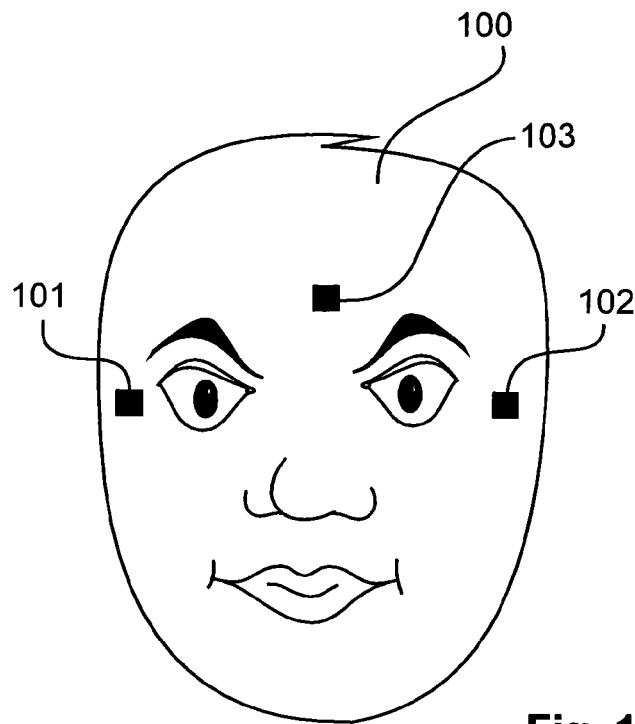
FIG. 1 shows an example of a horizontal EOG capture setup.

FIG. 1 shows an example of a horizontal EOG capture setup. Around the eyes of a user's head 100, two horizontal electrodes 101, 102 are attached to the left and right temple, and a reference electrode also referred to as ground electrode 103 is attached to the middle of the forehead.

From the electrodes 101, 102, 103, a horizontal EOG signal of the user is recorded at a sample frequency Fs of e.g. 200 Hz. As an alternative to being directly attached to the user's head, the electrodes could also be embedded in a dedicated device (e.g. eyeglasses) which touches the user's head at or near the desired positions during use.

Figure 2:
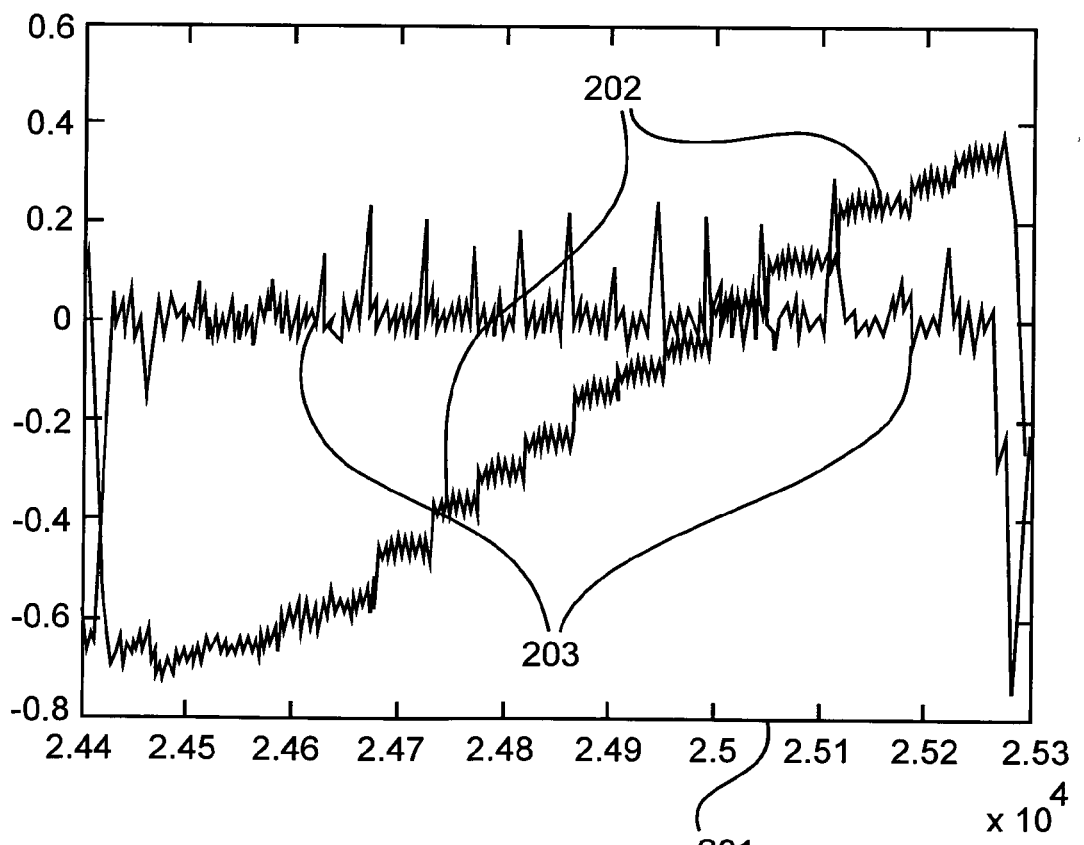
FIG. 2 shows an example calibrated horizontal EOG signal, as it arises while a user is reading one complete line of text; together with one wavelet level of detail signal thereof.

FIG. 2 shows, as a function of a sample index 201, an example calibrated horizontal EOG signal 202, as it arises while a user is reading one complete line of text; together with a third level of detail signal D3 thereof 203.

The horizontal EOG signal is amplified using an appropriate device (e.g. commercial instrumentation amplifiers for physiological recording) and is then processed. The processing step aims at determining and analyzing the horizontal eyes movements, and comprises the following steps:

First Step:
Calibration of the horizontal EOG signal s into a calibrated signal sn, in such a way that an amplitudes range of 1.0 in the calibrated signal sn corresponds to the entire text width.

Second Step:
The calibrated signal sn is subjected to a wavelet transform with a spline wavelet, on 5 levels of detail. The level of detail signals are named D1, . . . , D5. For the wavelet transform, the "À Trou" algorithm [9] or stationary wavelet transform can advantageously be used.

The wavelet transform is an advantageous approach to process EOG signals, because it allows a fast multi-bandpass filtering and constitutes a convenient way to identify fast transitions in the signal, especially the fast transitions that occur when the line of sight jumps to the beginning of a next line.

A dyadic wavelet transform may be used. However, other filtering techniques may also be used to perform a similar processing. As the core of the wavelet transform, a cubic spline wavelet may be used. In the "a trou" algorithm, no subsampling is applied to the signal, but the filter responses are upsampled instead with zero padding. This entails, among others, that the level of detail signals all have the same length than the original signal.

Conceptually, after such a wavelet transform, the first level of detail signal D1 contains the upper half of the normalized frequency range, corresponding to pi/2 to pi. The second level of detail signal D2 contains the second-lowest quarter of the normalized frequency range, corresponding to pi/4 to pi/2. The third level of detail signal D3 contains the second-lowest eighth of the normalized frequency range, corresponding to pi/8 to pi/4. The fourth level of detail signal D4 contains the second-lowest sixteenth of the normalized frequency range, corresponding to pi/16 to pi/8, and so on.

In a typical embodiment, it may be found empirically, that the sum of the third level of detail signal D3 plus the fourth level of detail signal D4 plus the fifth level of detail signal D5 constitutes the most useful frequency band to do the evaluations described here. This sum signal D3+D4+D5 may therefore also be termed the "informative signal". The first and second level of detail signals D1 and D2 may be found to contain mostly recording noise, and the sixth and higher level of detail signals D6, D7, . . . may be found to contain mainly physiological drift components.

As the impulse response core to be used in the wavelet transform, one may use
- a lowpass forward filter, commonly denoted as h[n], of length four, where the coefficients h[n]/sqrt(2) are (0.125; 0.375; 0.375; 0.125);
- a lowpass backward filter, commonly denoted as h~[n], of length four, where the coefficients h~[n]/sqrt(2) are (0.125; 0.375; 0.375; 0.125);
- a highpass forward filter, commonly denoted as g[n], of length two, where the coefficients g[n]/sqrt(2) are (−0.5; 0.5); and
- a highpass backward filter, commonly denoted as g~[n], of length six, where the coefficients g~[n]/sqrt(2) are (−0.03125; −0.21875; −0.6875; 0.6875; 0.21875; 0.03125). These are also termed quadratic spline filters.

A dyadic wavelet transform, used on signal blocks of 512 samples, has a total of 9 levels. Of these, the last level signal D9 contains the very lowest frequencies. This shows, that in such a context, an informative signal composed of D3+D4+D5, conceptually has a bandpass character.

FIG. 2 shows, as a function of a sample index 201, an example calibrated horizontal EOG signal 202. That the signal is calibrated can be seen from the fact that the signal comprises amplitudes in the range of about −0.7 to +0.3, corresponding to an amplitude range of 1. FIG. 2 also shows a medium level of detail component 203 of the example calibrated horizontal EOG signal 202 which corresponds to the level D3 thereof.

Third Step:

A currently read line Li is detected as being a portion of the gaze signal delimited by two line delimiters Li0 and Li1. The Line delimiters are defined as those time samples where sd=D3+D4+D5, i.e. the sum of the third level of detail signal, the fourth level of detail signal, and the fifth level of detail signal of the wavelet transformed signal is under a fifth threshold Tline, and where additionally in a time window of a width Wline preceding the time sample, no other line delimiters exist.

Figure 6:
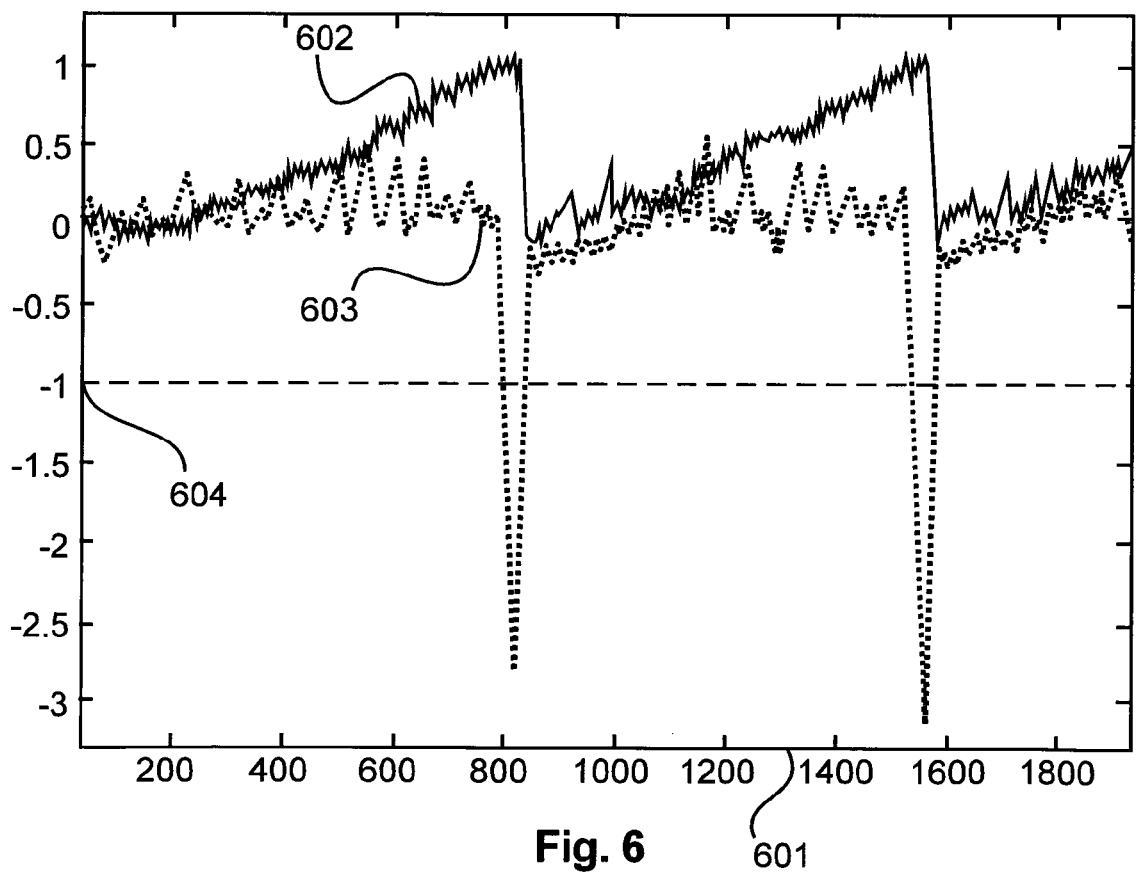
FIG. 6 shows a calibrated horizontal EOG signal together with the sum of the third to fifth level of detail signals thereof.

In the example setting, the fifth threshold Tline equals −1 and Wline equals the number of samples corresponding to a duration of 0.5 seconds, typically. FIG. 6 shows, as a function of the sample index 601, a calibrated horizontal EOG signal 602 together with the sum 603 of the third to fifth level of detail signals thereof. The EOG signal has values smaller than the fifth threshold Tline=−1 604 only during those portions where—at a line wrap—the gaze quickly moves back to the beginning of the next line.

Fourth Step:

A current reading speed Vi is calculated from the sampling frequency Fs and the sample indexes Li0, Li1 of the line delimiters surrounding the current line, as Vi=Fs/(Li1−Li0). The current reading speed can be measured in lines per second.

Fifth Step:

A positive saccade count Sip is counted on the interval [Li0,Li1] as the number of time samples where a second highest frequency component D4 of the wavelet transformed signal is above a sixth threshold Tsaccade, and where additionally in a time window of a width Wsaccade preceding the time sample, no other saccades time sample exists.

A negative saccade count Sin is counted on the interval [Li0,Li1] as the number of time samples where a second highest frequency component D4 of the wavelet transformed signal is below a threshold of (−1)*Tsaccade, and where additionally in a time window of the width Wsaccade preceding the time sample, no other saccades time sample exists.

In the example setting, Tsaccade equals 0.02 typically; Wsaccade equals the number of samples corresponding to 0.2 seconds, typically; and a time sample is considered as a saccades time sample, if its magnitude is greater than Tsaccade, with other words if its value is either below (−1)*Tsaccade or above Tsaccade.

Then, a number of saccades Si in the currently read line is calculated as the difference between the positive saccade count Sip and the negative saccade count Sin:

$$Si=Sip-Sin$$

This calculation takes care of the fact that while reading a text, the gaze sometimes jumps back and forth to re-read a portion of text, in order to reinsure the meaning of something that was perhaps too hastily read in the first instance.

Sixth Step:

If the number of saccades Si is above a second threshold Nmax, or if the reading speed Vi is below a third threshold Vmin, this is detected as an indicator that the currently used font size is too small, and an increase of the font size, e.g. to a next bigger available font size, is initiated. This will be denoted as a too small font size status in the following.

In this, the second threshold Nmax equals 20 typically, and the third threshold Vmin equals 0.05 lines per second, typically.

On the other hand, if the number of saccades Si is less than a fourth threshold Nmin, this is detected as an indicator that the currently used font size is too big, and a decrease of the font size, e.g. to a next smaller available font size, is initiated. This will be denoted as a too big font size status in the following.

In this, the fourth threshold Nmin equals 15 typically.

With other words, if Nmax≤Si (Nmax=20 typically) or Vi≤Vmin (Vmin=0.05 second per line typically), increase the font size of one step. Else if Si≤Nmin (Nmin=15 typically), decrease the font size of one step.

Seventh Step:

The third to sixth step are repeated for every consecutive text line. Each time, the text line index i is increased by 1.

Figure 3:
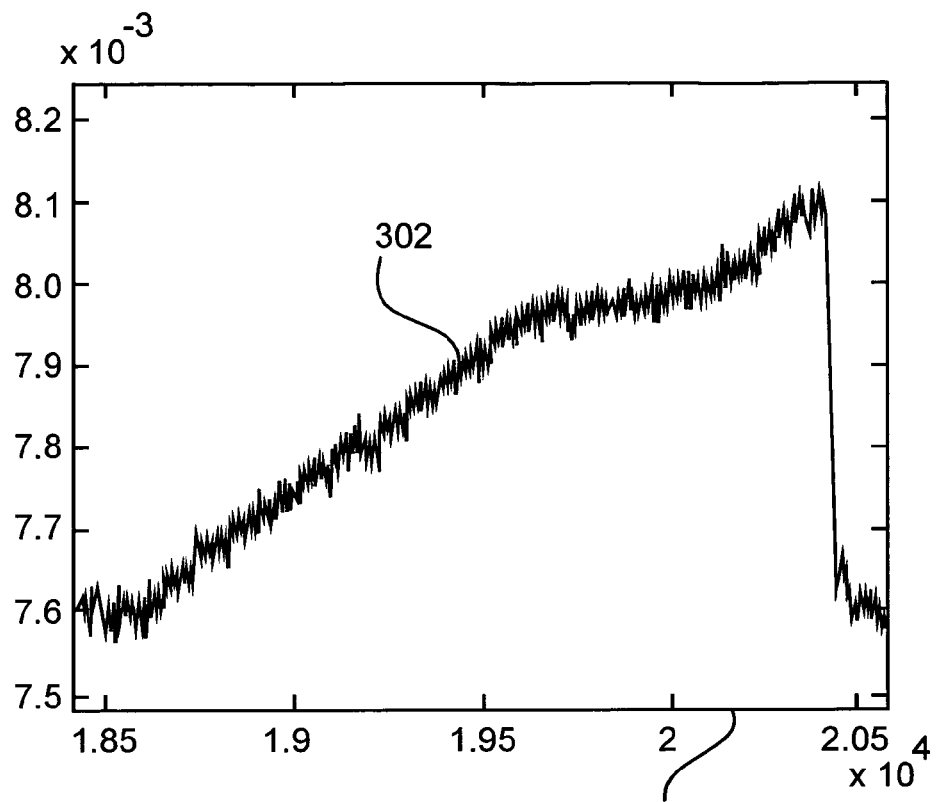
FIG. 3 shows a raw EOG signal in a setting with a very small font size.
Figure 4:
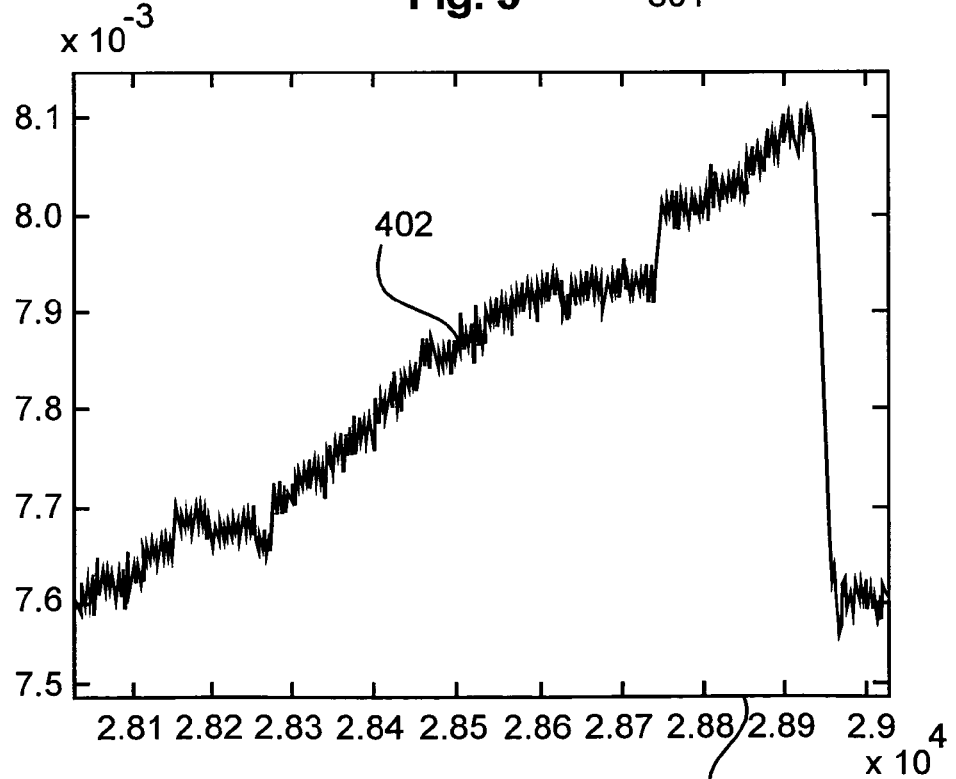
FIG. 4 shows a raw EOG signal in a setting with an "optimal" font size.
Figure 5:
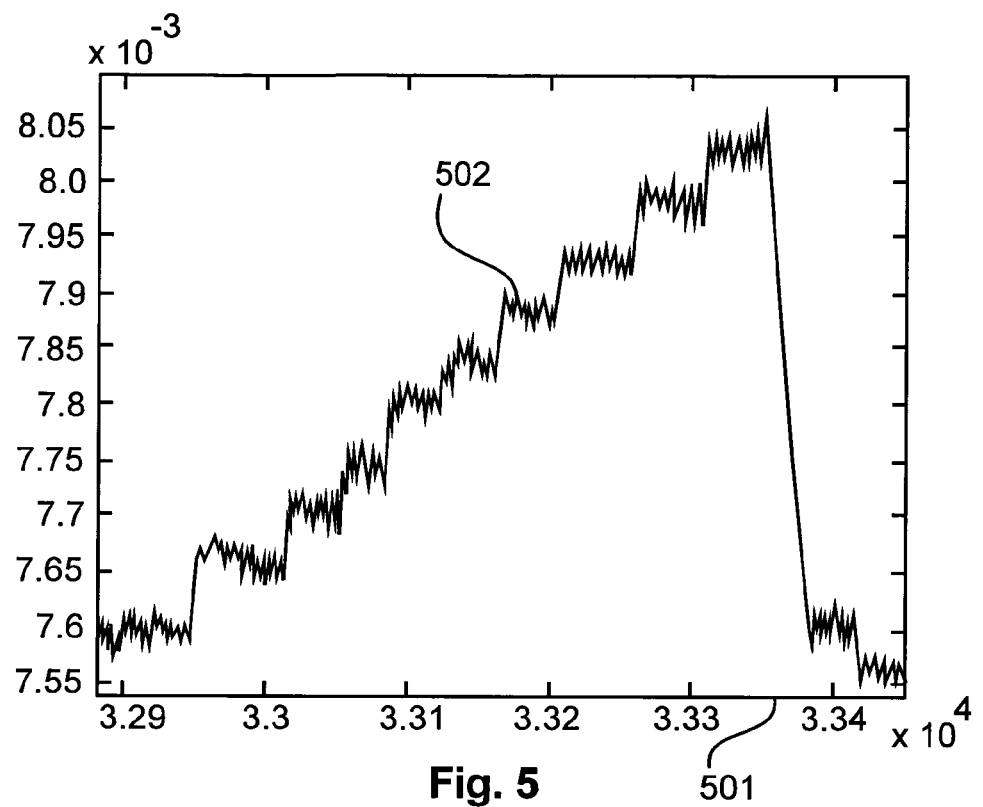
FIG. 5 shows a raw EOG signal in a setting with a very big font size.

FIG. 3 shows, as a function of the sample index 301, an uncalibrated EOG signal 302 in a setting with a very small font size. FIG. 4 shows, as a function of the sample index 401, an uncalibrated EOG signal 402 in a setting with an "optimal" font size. FIG. 5 shows, as a function of the sample index 501, an uncalibrated EOG signal 502 in a setting with a very big font size. The methods according to this invention iteratively allow to switch from extreme configuration (very little or very big font size) to the optimal one. Note that the notion of "optimal" font size may be user-dependent and can be adjusted by allowing the user to modify the thresholds Nmin, Nmax, and Vmin.

It can be seen as advantageous about this invention, that it improves the visual comfort on media like computers, TV or e-books. This leads to reduced eyestrain because the eyes don't move more than necessary and because the deciphering phenomena is limited. User satisfaction is increased because the size of the font is automatically adapted. And it provides a better understanding of text content because of a good fluidity while reading.

REFERENCES

[1] Young L R, Sheena D (1988): Eye-movement measurement techniques. In Encyclopedia of Medical Devices and Instrumentation, ed. J G Webster, pp. 1259-1269, John Wiley, New York.
[2] L. Y. Deng, C. Hsu, T. Lin, J. Tuan, Y. Chen: EGG-Based Signal Detection And Verification For HCI. In 2009 International Conference on Machine Learning and Cybernetics, Volume 6, pp. 3342-3348.
[3] International Society for Clinical Electrophysiology of Vision (ICSEV), "Visual Electrodiagnostics—A Guide To Procedures", http://www.iscev.org/standards/procedures-guide.html.
[4] H. Miyashita, M. Hayashi, K. Okada: Implementation of EGG-based Gaze Estimation in HMD with Head-tracker. In 18th International Conference on Artificial Reality and Telexistence (ICAT 2008).
[5] Tobii, "Tobii unveils the world's first eye-controlled laptop", http://www.tobii.com/en/eye-tracking-integration/global/news-and-events/press-releases/tobii-unveils-the-worlds-first-eye-controlled-laptop/.
[6] EagleEyes Project, Boston College, http://www.bc.edu/schools/csom/eagleeyes/faq.html
[7] A. Bulling, J. A. Ward, H. Gellersen, G. Tröster: Eye Movement Analysis for Activity Recognition Using Electrooculography. In IEEE Transactions on Pattern Analysis and Machine Intelligence, vol. 33, no. 4, pp. 741-753, April 2011.
[8] Single Line Reader, L. E. L. Mizutan, T. Nakajima, Graduate School of Educational Informatics—Tohoku University—Japan, http://www.cmsoft.com.br/slr/.

[9] M. J. Shensa: The Discrete Wavelet Transform: Wedding the À Trous and Mallat Algorithms. In IEEE Transactions on Signal Processing, Vol. 40 No. 10, pp. 2464-2482, October 1992.

The invention claimed is:

1. A method for gaze-controlled text size control, comprising:
    probing, sampling and recording a user's horizontal gaze signal at a predefined sampling frequency;
    subjecting the horizontal gaze signal to a frequency or wavelet transform on several levels;
    detecting, in the transformed horizontal gaze signal, line delimiters;
    deriving, for each pair of consecutive line delimiters enclosing the transformed horizontal gaze signal of a current line, a reading speed from the distance in samples of the pair of line delimiters, in relation to the sampling frequency of the horizontal gaze signal;
    determining, from the transformed horizontal gaze signal of the current line, a number of saccades in the current line, by counting those locations, where the horizontal gaze signal has a sudden high slope portion surrounded on both sides by portions of markedly smaller slope, and wherein the number of the saccades is determined by determining a positive saccade count, determining a negative saccade count, and calculating the number of saccades as a difference between the positive saccade count and the negative saccade count; wherein
    an increase of the font size is initiated if the number of saccades is above a first threshold or if the reading speed is below a second threshold, and a decrease of the font size is initiated if the number of saccades is less than a third threshold.

2. A method for gaze-controlled text size control, comprising:
    probing, sampling and recording a user's horizontal gaze signal at a predefined sampling frequency;
    subjecting the horizontal gaze signal to a transform;
    detecting, in the transformed horizontal gaze signal, line delimiters;
    deriving, for each pair of consecutive line delimiters enclosing the transformed horizontal gaze signal of a current line, a reading speed from the distance in samples of the pair of line delimiters, in relation to the sampling frequency of the horizontal gaze signal;
    determining, from the transformed horizontal gaze signal of the current line, a number of saccades in the current line, by counting those locations, where the horizontal gaze signal has a sudden high slope portion surrounded on both sides by portions of markedly smaller slope; wherein
    an increase of the font size is initiated if the number of saccades is above a first threshold or if the reading speed is below a second threshold, and a decrease of the font size is initiated if the number of saccades is less than a third threshold; and
    wherein the horizontal gaze signal, before the detecting of the line delimiters, is calibrated in such a way that an amplitude difference of 1 in the calibrated signal matches width of text being read.

3. The method of claim 2 wherein the transform subjected to by the horizontal gaze signal is a frequency transform.

4. The method of claim 2 wherein the transform subjected to by the horizontal gaze signal is a wavelet transform.

5. The method of claim 3 wherein line delimiters are detected by locating pieces of the transformed horizontal gaze signal where selected ones of frequency bands are below a threshold.

6. The method of claim 4 wherein line delimiters are detected by locating pieces of the transformed horizontal gaze signal where selected ones of wavelet levels of detail are below a threshold.

* * * * *